United States Patent [19]

Storace

[11] Patent Number: 5,100,041

[45] Date of Patent: * Mar. 31, 1992

[54] SURGICAL STAPLER

[75] Inventor: Anthony Storace, Norwalk, Conn.

[73] Assignee: Technalytics, Inc., Montvale, N.J.

[ * ] Notice: The portion of the term of this patent subsequent to Apr. 24, 2007 has been disclaimed.

[21] Appl. No.: 440,242

[22] Filed: Nov. 22, 1989

Related U.S. Application Data

[62] Division of Ser. No. 164,818, Mar. 7, 1988.

[51] Int. Cl.⁵ .............................................. A61B 17/00
[52] U.S. Cl. ...................................... 227/19; 227/116; 227/121; 227/901; 606/219
[58] Field of Search .................. 227/19, 116, 121, 901, 227/DIG. 1; 606/219

[56] References Cited

U.S. PATENT DOCUMENTS

| 4,582,237 | 4/1986 | Storace et al. | 227/19 |
| 4,645,111 | 2/1987 | Larrabee et al. | 227/19 |
| 4,664,305 | 5/1987 | Blake, III et al. | 227/19 |
| 4,669,647 | 6/1987 | Storace | 227/19 |
| 4,796,793 | 1/1989 | Smith et al. | 227/19 |
| 4,919,320 | 4/1990 | Storace | 227/19 |

Primary Examiner—Robert A. Hafer
Assistant Examiner—Kerry Owens
Attorney, Agent, or Firm—Rosen, Dainow & Jacobs

[57] ABSTRACT

A surgical stapler which closes a staple during the downstroke of the former and strips the closed staple during the upstroke of the anvil by pressing the cross-arm of the closed staple against a bevelled cam surface.

11 Claims, 7 Drawing Sheets

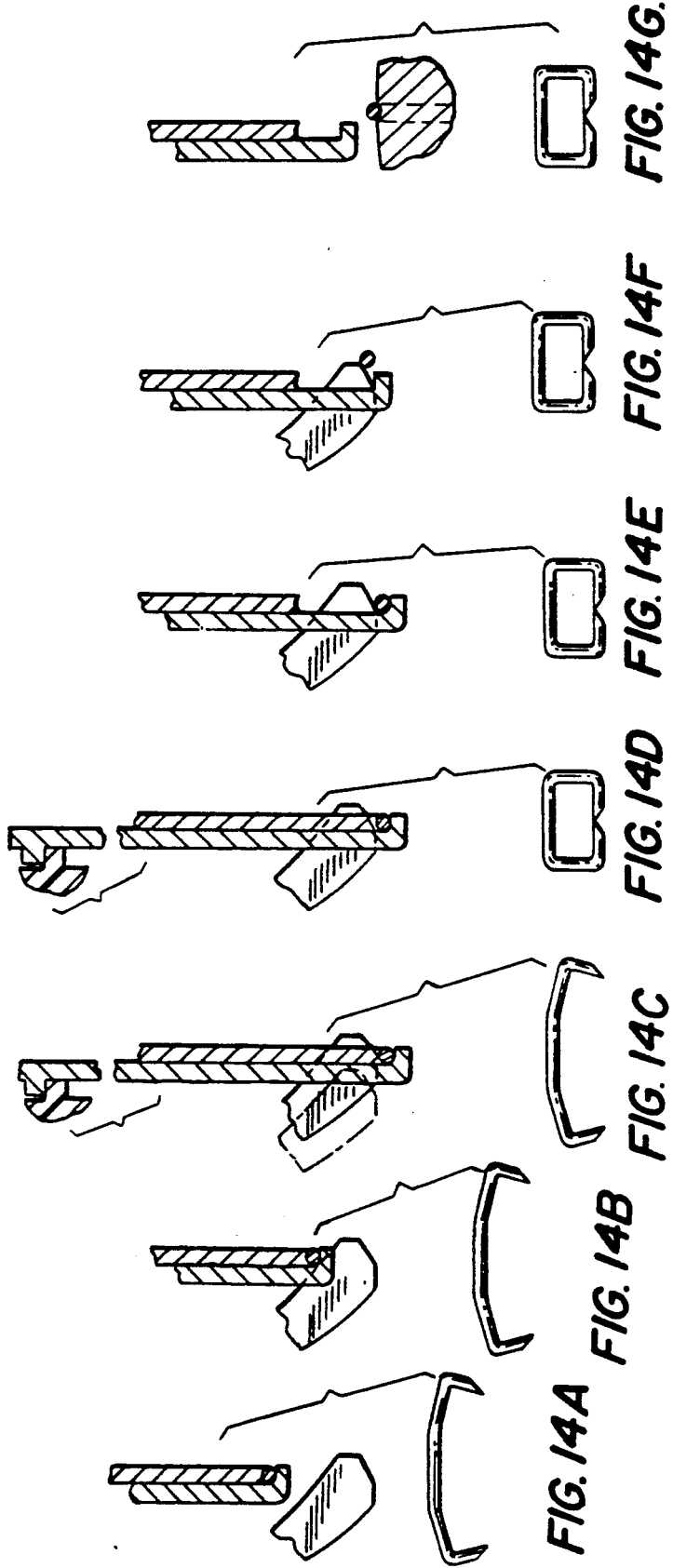

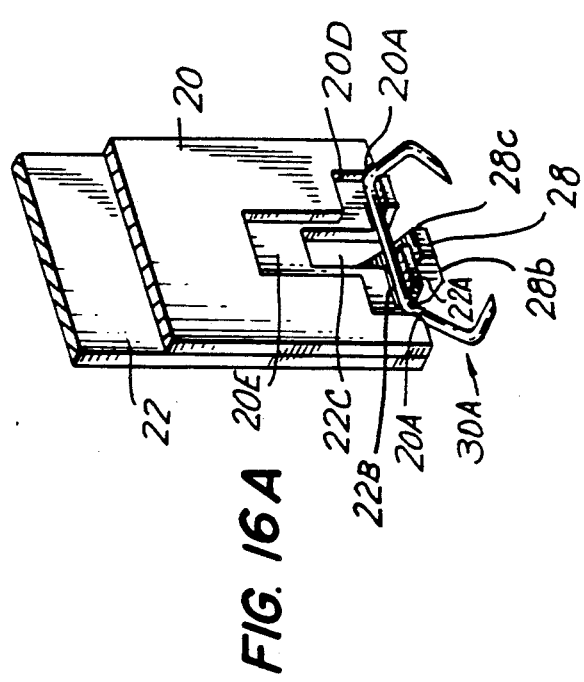

SURGICAL STAPLER

This is a division of application Ser. No. 164,818, filed March 7, 1988.

BACKGROUND OF THE INVENTION

This invention is in the field of surgical staplers and staple guns for implanting surgical staples. More particularly, this invention concerns the mechanism for controlling the staple during descent and closure and for causing release and separation of the closed staple from the stapler.

Numerous prior art staplers have been developed, each using a staple having an initial open state followed by closure to a formed or closed configuration. In these staplers, typically each staple is positioned upon an anvil which supports the staple's crossarm or crossbar with the staple's sharply pointed legs extending generally downward. Force from the former bends the staple until a rectangular or other generally closed polyganic configuration is achieved. For all these staplers the final step following closure is release or stripping of the staple from the stapler. In many staplers the release is not reliable or not quick or not smooth or combinations of the above. When a complete clean release fails to occur the staple which is closed in the incision remains attached to stapler. The surgeon must then either manipulate the stapler in different directions trying to separate the staple either from the stapler or from the wound, or he may pull on the trigger again, which is likely to force a second staple onto the stuck one causing a worse jam or hang-up of the device.

Where the staple remains engaged in the stapler, the surgeon will, because the tissue is soft, usually be able to manipulate the stapler until the staple pulls free of the tissue; however, the staple hang-up scenario described above is an inconvenience at best and may be a critical delay in the wound or incision closure process. From a commercial consideration many surgeons refuse to use staplers which have a reputation for unreliable closure and/or release.

The reasons for failure of staplers to reliably release are many, obviously depending on the individual stapler. In the typical case a former element presses with substantial force that bends a staple about an anvil element. The formed staple then tends to adhere to the former because the latter maintains the staple closed against spring-back force of the staple trying to open. The staple also tends to adhere to the anvil because of being bent tightly around the anvil lip. Finally staples may jam in passageways due to dimensional tolerance that are either too tight or too loose. Attempts to release or strip the staple must overcome the frictional forces created between the former and/or the anvil with this closed staple.

The focus herein is primarily on staplers of the type described in U.S. Pat. Nos. 4,582,237 and 4,669,647 which patents are incorporated by reference into this specification. In these particular prior art patents the staplers have a "moving anvil" which is caused to descend while it carries an open staple to a position below the housing where more visible closure occurs. Some other relevant prior art staplers have "fixed" anvils situated at one predetermined elevation. Stripping of the formed staple in these various prior art devices occurs during the final downward movement of the former at which time one or more of the above-described frictional forces must be overcome by a stripping element on the former. Typically the anvil remains at its originally fixed or descended elevation with the closed staple thereon, or more specifically, with the anvil's lip extending beneath the central part of the staple's crossarm. The former is then caused to descend slightly further with a bevelled edge of the former camming the staple's crossarm transversely off the anvil's lip.

The above type of stripping mechanism, while appearing seemingly simple, has been found unreliable to produce a reliable and clean release of the closed staple. In part the frictional forces interfere with smooth operation. Attempts at solutions included tightening dimensional tolerances which resulted in substantial cost increases, or seeking to reduce friction by a less tightly closed staple which was equally unsatisfactory.

Also, in relevant prior art staplers other unsatisfactory features include a tendency of the staple's crossarm to bow upward during closure, and/or a tendency for the staple to move from its proper position orientation during descent.

The stapler of the new invention provides significant improvements in all these areas as described below. The present invention approaches the stripping problem from a totally different point of view, thus providing a stripping mechanism that has numerous advantages over the prior-disclosed stripper, along with improvements in the other features discussed above.

SUMMARY OF THE INVENTION

This invention is an improved surgical stapler which has a new structure and method for delivering, closing and releasing or stripping a closed or formed staple. A principle difference of the new stripper mechanism from prior art strippers, such as the ones disclosed in U.S. Pat. Nos. 4,582,237 and 4,669,647, is that stripping now occurs during the return stroke of the former and anvil in combination with a new flex-tab as contrasted with stripping at the end of the forward stroke of the former by a blade portion of the former itself. The new apparatus provides a variety of additional benefits and improvements as described below over known prior staplers.

A first new features of this invention is the flex-tab which permits greater ease and reliability of the stripping operation. This flex-tab has a tip part which resiliently extends above the staple's crossarm before the staple is closed. After the staple is closed and the former begins to rise, the anvil lips also rise urging the crossbar against a bevelled lower surface of the new flex-tab. In this stage the flex-tab is relatively stiff and does not flex away, so that its bevelled lower surface cams the crossbar transversely and thus drives the staple off the anvil. Since stripping occurs on the return stroke of the former and anvil instead of on the former's downstroke, the surgeon can use the stapler to better position the tissue for the next forceps action at the end of the downstroke. With prior devices, release occurred at the end of the downstroke, and thus positioning tissue for the next forceps action was not very effective.

A second beneficial feature and improvement of the new invention herein is the provision for "crowning" the staple upon formation thereof. In typical prior staplers the crossarm or transverse crossbar of the staple between its pair of descending legs, tends to bow upward as the staple is bent to its closed state. It is preferable to set or crown the top of the closed staple as this reduces the elastic after-effect known as spring-back. This setting or crowning tends to produce formed staples with minimum point gaps which reduces the possibility of the staple being dislodged from the closure.

The uncrowned staple configuration is inferior to a more rectangular shape, because the pointed legs extend at an angle which is less secure than generally parallel to the skin surface; also a bowed crossarm will be less effective in maintaining the proximation of the adjacent joined edges of tissue in a flat plane for a smooth closure. In some prior art devices, this problem was solved by an additional support element on the anvil; however, the present invention designates the new flex-tab itself to serve the additional function of providing this crossarm support. Accordingly, the anvil structure is simplified and a former part is omitted.

With the new crowning feature, the action of inserting a staple stops momentarily at the end of the forward stroke of the former when the staple is fully formed. This moment may be used by the surgeon to plan the placement of the next staple before the last closed staple is released. This is a useful benefit of the new structure that will render it more practical.

A third advantage is a staple track or guide during the last portion of the staple's descent to maintain it centered on the anvil and to help prevent it from tipping. This cooperates with downward extending tabs on the anvil to prevent tipping about the axis of the crossarm.

A fourth advantage in the new invention is its reduced sensitivity to dimensional tolerances. Such apparatus is less expensive to manufacture and more reliable to use, both of these benefits being critical for a product to be considered for serious commercialization.

In the operation of the new stapler and the new stripper mechanism the former drives the staple against the anvil lip and drives both downward until the central part of the staple engages and cams the flex-tab out of the way. Immediately afterward, the flex-tab springs back above the crossarm. During the initial descent of the former the anvil remains undescended. This occurs because the anvil spring is stiffer and maintains the anvil up (undescended) while the former's descent compresses the weaker former spring.

In the prior art stapler this relationship of the anvil spring being stiffer than former spring was a constant, e.g. remained true at all times. After the former's initial descent, it and the staple forceably drove the anvil downward, thus overcoming the anvil spring's resistance. The staple was then formed and stripped during the final phase of the former's downstroke. Finally, upon release of the trigger the stronger anvil spring drove the anvil and former upward until the anvil's travel was stopped by an upstop; then the former spring continued to drive the former to it's own upstop position.

As discussed above, the prior stripper operated at the end of the downstroke whereby a bevelled edge of the former cammed the closed staple laterally off the anvil lip. Then the stronger anvil spring drove the anvil and former upward until the anvil reached its upstop and the former continued upward to its own unstop.

In this new device stripping-off of the closed staple is achieved when the trigger is relaxed/released and the former begins to rise out of engagement with the formed staple while the anvil remains at its down position. For this to occur, the former spring has to be stronger than the anvil spring at that moment. In this new arrangement the former spring is initially weaker than the anvil spring, but becomes stiffer as it is compressed, until it becomes stronger than the anvil spring during staple formation. The details of actual spring forces achieved are explained more specifically in the description of the preferred embodiment.

Upon release of the trigger, the now-stronger former spring drives the former upward overcoming the now weaker anvil spring tending to drive the anvil upward so that the former rises while the anvil remains forced against its downstop. The initial upward movement of the former tends to separate the former's drive surfaces from the outer surfaces of the closed staple, overcoming the friction therebetween. With this partial ascent of the former, the expanded former spring becomes essentially equal to the anvil spring, and the anvil then rises with continued rise of the former.

At this moment the closed staple is barred from rising by the flex-tab which became repositioned immediately above and adjacent the top of the staple after it was driven down onto the anvil lip. The upward movement of the anvil urges the top surface of the closed staple against the bevelled lower surface of the flex-tab which cams or strips the staple laterally off the anvil lip. This stripping phase occurs easily and smoothly, since the former has already been lifted off of and out of contact with the staple. A slight variation may occur where the staple is not tightly bound around the anvil lips, and the ascending former's drive surfaces drag the staple. The staple's crossarm is thus urged against the flex-tab and cammed off the anvil lips and released. Finally, the former and anvil return upward to their respective upstops as described with respect to the prior art stapler.

BRIEF DESCRIPTION OF THE DRAWINGS

FIGS. 14A-14G are schematic views showing the stages of the downstroke and the upstroke of the former and anvil.

FIGS. 15A and 15B are side views of the flex tab.

FIGS. 16A and 16B are schematic perspective views showing the stages of the downstroke and upstroke of the former and anvil.

FIG. 17 is a front elevational view of a prior art staple.

DETAILED DESCRIPTION OF THE PREFERRED EMBODIMENT

The invention herein is a new surgical stapler with an improved mechanism for delivering, forming and releasing a closed staple. This invention is applicable: (a) for staplers with descending anvils of the type disclosed in U.S. Pat. Nos. 4,582,237 and 4,669,647, which patents are incorporated herein by reference; (b) for staplers of other types, particularly those having fixed anvils as contrasted with the moving, descending anvils of the patents cited above; (c) for staplers with rotating heads; and (d) for staplers which rotate the open staple before it is formed.

Figure 6:
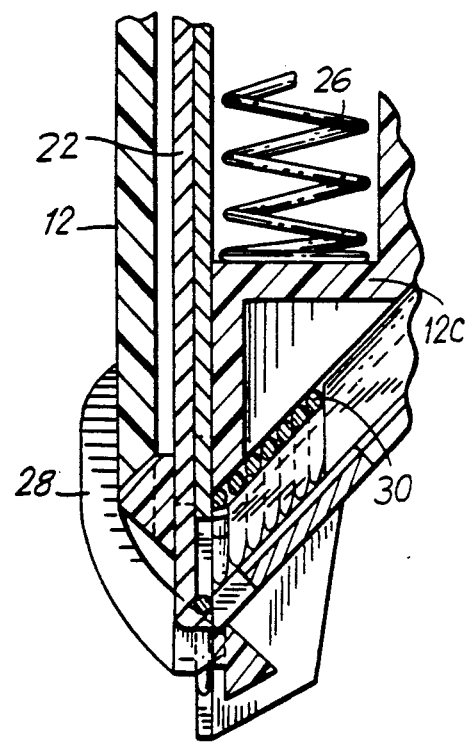
FIG. 6 is a fragmentary sectional elevation view of FIG. 5.

In the present invention it is contemplated that a staple such as the one seen in FIG. 6 of said prior art patents and reproduced as FIG. 17 in this application, would be used; however, staplers using staples of other configurations could also be adapted to utilize one or more features of the present invention.

A. Parts of the New Stapler

Figure 1:
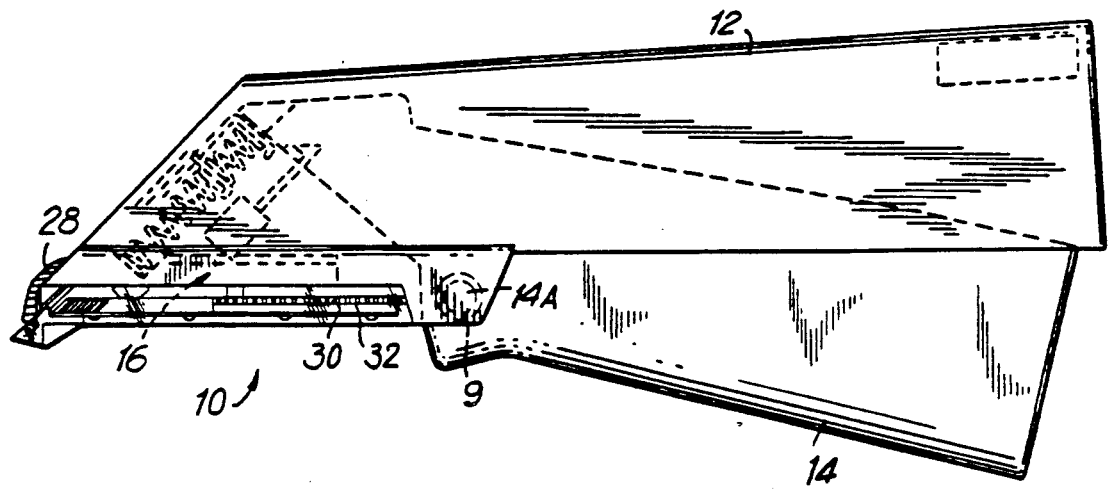
FIG. 1 is a side elevational view showing the new surgical stapler invention.

The preferred embodiment of the present invention is illustrated first as a complete assembled stapler 10 in FIG. 1, having as its main components, casing 12, trigger 14, and a staple cartridge 15 and forming subassembly 16. This subassembly, shown in greater detail in FIG. 3, includes frame 18, former 20, anvil 22, former spring 24, anvil spring 26, and flex-tab 28, the last named element serving a number of different functions.

Figure 3:
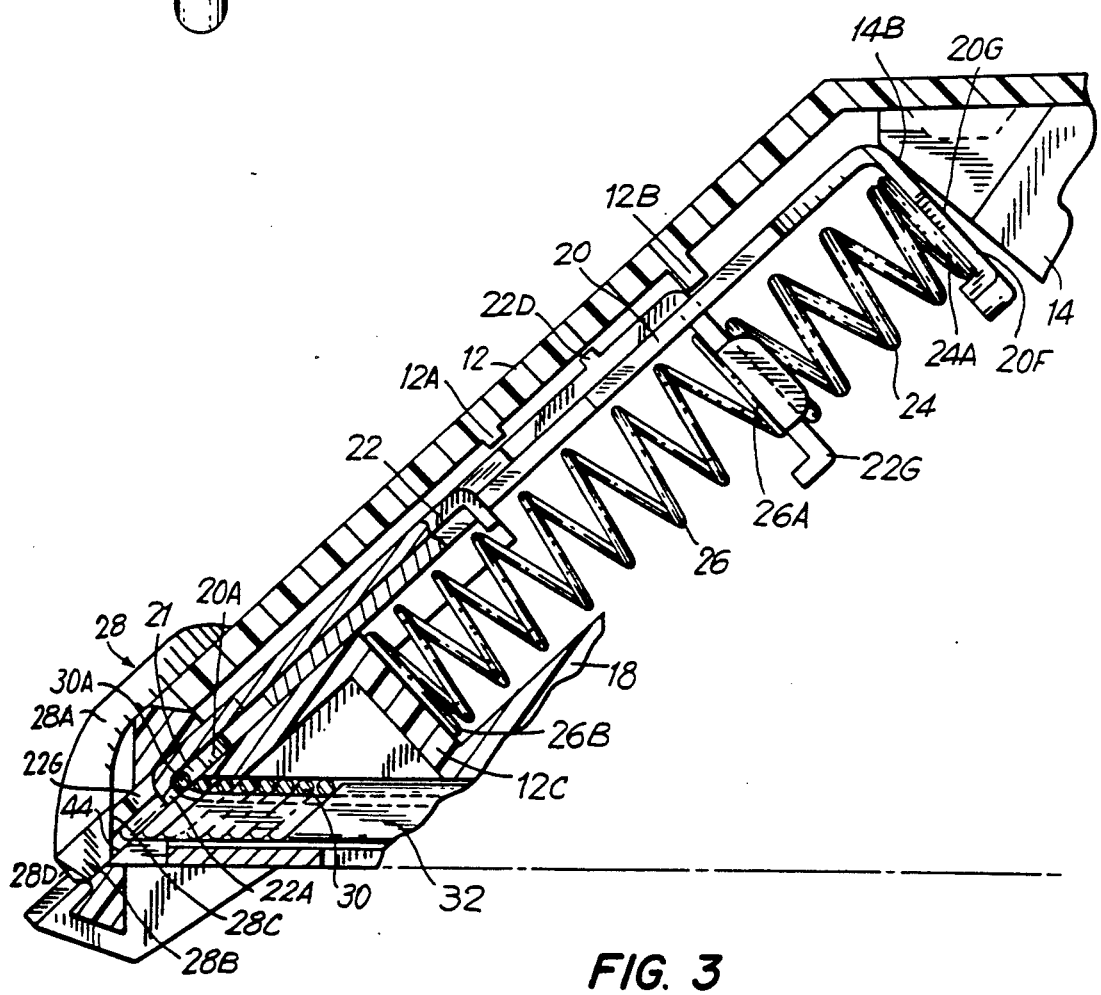
FIG. 3 is a fragmentary sectional view taken along line 3—3 of FIG. 2.

The trigger 14, shown in FIGS. 1 & 3, and the casing 12 are molded parts, preferably of plastic such as polycarbonate. During assembly the casing walls 13 are merely elastically deflected outward and apart from each other, and the trigger 14 and subassembly 16 are snapped in, with the pivot projections 14A of the trigger becoming securely but pivotably engaged in corresponding recesses 9 in the casing.

Figure 2:
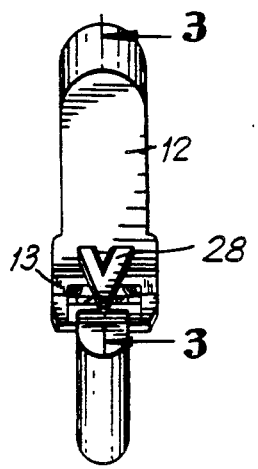
FIG. 2 is a front elevational view of the stapler of FIG. 1.

Staples 30 on a mandrel 32 in the cartridge 15 are urged by spring means (not shown) toward the anvil, similarly as is done and shown in FIGS. 2 and 17B of U.S. Pat. No. 4,582,237 referred to above.

The lower section of the former 20 has three parts with separate functions, as seen in FIGS. 3, 4, 5, 7, 16A and 16B. The lowest part comprises forming or drive surfaces 20A of the forming fingers 20B that engage and bend the top of a staple as later described. Within fingers 20B is a recess 20C whose inner-facing walls 20D engage and maintain end portions of the staple's crossarm as they are bent when the former moves downward relative to the stopped anvil which supports the staple's cross-arm. Above recess 20C and concentrically centered therewith is a further and higher recess 20E which allows clearance for the tip of the flex-tab when the former 20 moves during its downstroke. At the top end of the former is arm 20F whose underside engages the top end 24A of the former spring and whose top side 20G is engaged and driven by the drive end 14B of the trigger.

Figure 4:
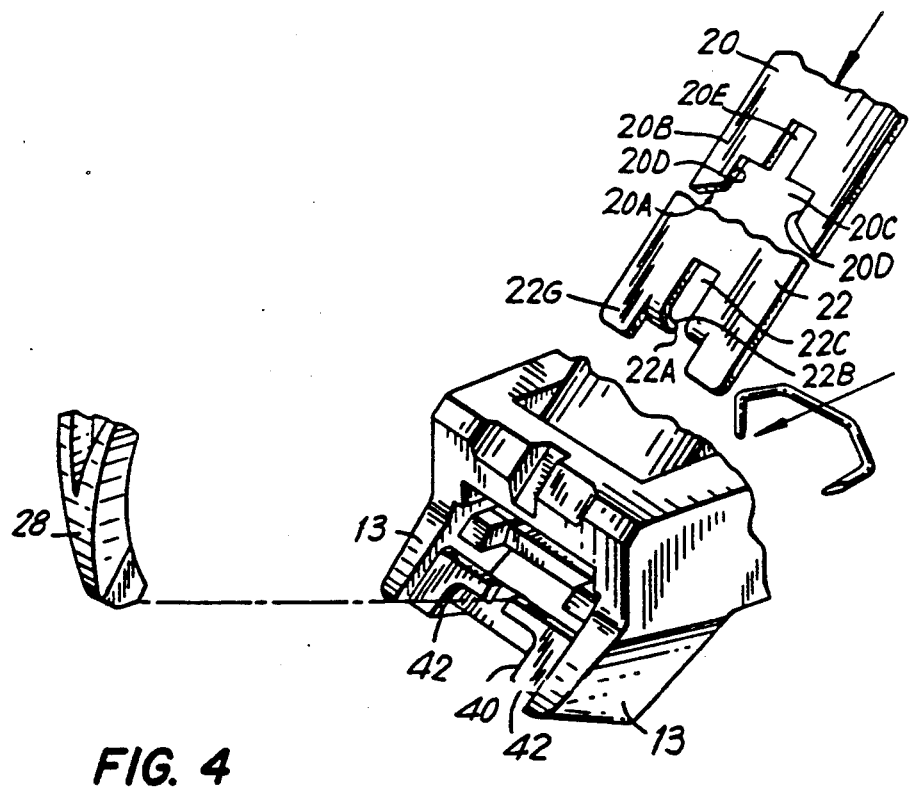
FIG. 4 is a fragmentary front perspective view of the stapler of FIGS. 1-3.
Figure 7:
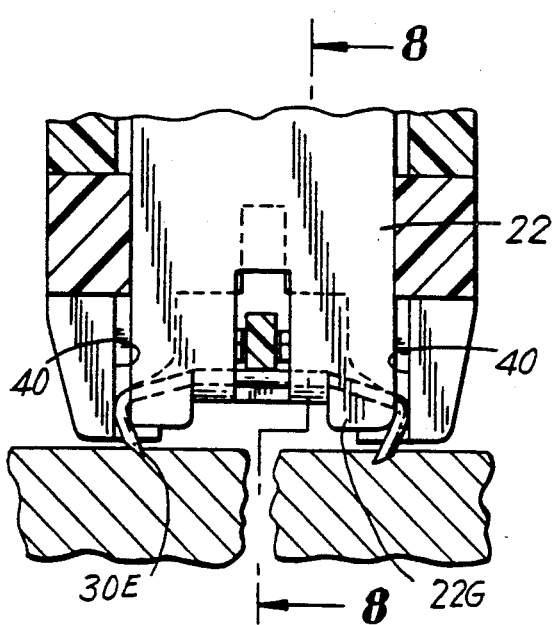
FIG. 7 is a fragmentary front elevational view similar to FIG. 5, with the staple and anvil driven downward by the former to an elevation below the flex-tab.

As seen in FIGS. 3, 4, 7, 16A and 16B, anvil 22 has a pair of spaced apart lips 22A having upper support surfaces 22B and with a recess 22C extending upward to provide clearance for the flex-tab when the anvil descends during forming of the staple. At the top end of the anvil is projection 22D for engaging the anvil's downstop 12A and upstop 12B shown schematically in FIG. 3. Also the anvil has arm 22G for engaging the top 26A of the anvil spring 26. As seen in FIGS. 3, 4 and 7 the anvil has guide tabs 22G for preventing forward tilt of the staple legs during descent and closure.

The staple 30A in FIGS. 16A and 17 has its crossarm or crossbar 30B, upper legs 30C diverging downwardly, lower legs 30D converging downwardly, and tips 30E. As seen schematically in FIG. 17, central area 30F of the crossarm 30A is engaged by the tip 28B of the flex-tab, middle areas 30G of the crossarm are supported by the anvil lips 22A, and outer areas 30H of the crossarm are engaged by the former's drive surfaces 20A.

The flex-tab 28 is fixed in elevation relative to the movable former and anvil. In this preferred embodiment the flex-tab, as seen in FIGS. 1-4, 6, 16A and 16B, is a molded part of the casing 12 and extends as a resilient curved arm 28A terminating as a tip 28B that is positioned generally in alignment with the staple and former. The tip has a bevelled top surface 28C and bevelled lower surface 28D.

B. Downstroke Operation

Prior to the beginning of the downstroke of the former, a small space 21 exists between the top surface 22B of the anvil lip and the bottom surface 20A of the former's fingers as seen in FIG. 3 and exaggerated in FIG. 16A. The lead staple 30A is delivered from its mandrel onto said top surface 22B of the anvil lip 22A. As the trigger is squeezed and the former's downstroke begins, the former's lower surfaces 20A quickly engage the top of the staple 30A, and then as a subassembly the former 20, staple 30A and anvil 22 begin to descend together.

Figure 5:
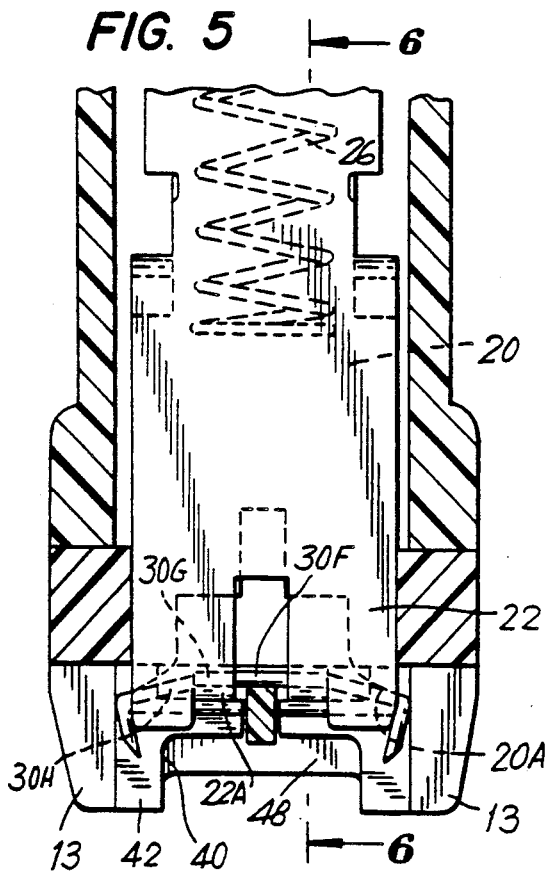
FIG. 5 is a fragmentary front elevational view of the stapler showing the former lowered to engage the staple's crossarm upon the anvil lips, with the flex-tab also beneath the center of the staple's cross-arm.

As seen in FIGS. 16A, 17 and 5, as the former's drive surfaces 20A press downward on the outer surfaces 30H of the staple's crossarm 30B, the middle portions 30G are supported by the anvil lips 22A, and the central part 30F of the cross-arm engages the beveled top surface 28C of the flex-tab 28.

Figure 8:
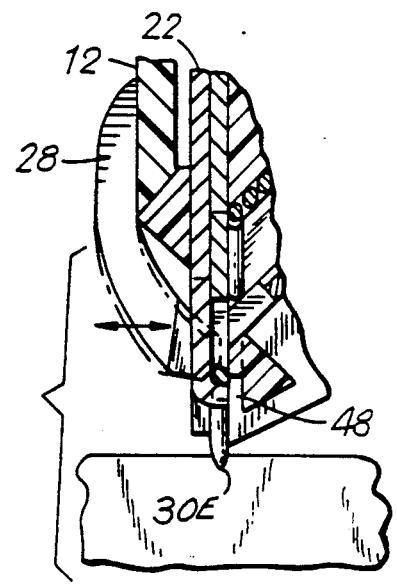
FIG. 8 is a fragmentary sectional elevation view of FIG. 7. the dotted line indicates the flexed position of the flex-tab when the staple cams the flex-tab forward.
Figure 9:
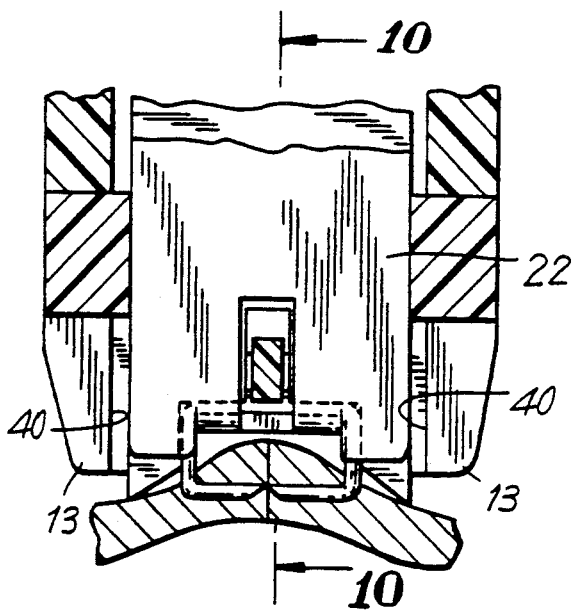
FIG. 9 is a fragmentary front elevational view similar to FIG. 7, with the former further descended and the staple formed to its closed configuration.
Figure 10:
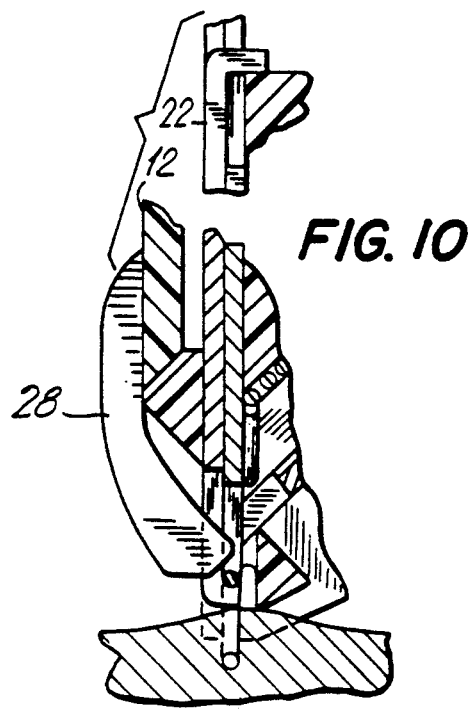
FIG. 10 is a fragmentary sectional elevation view of FIG. 9.
Figure 11:
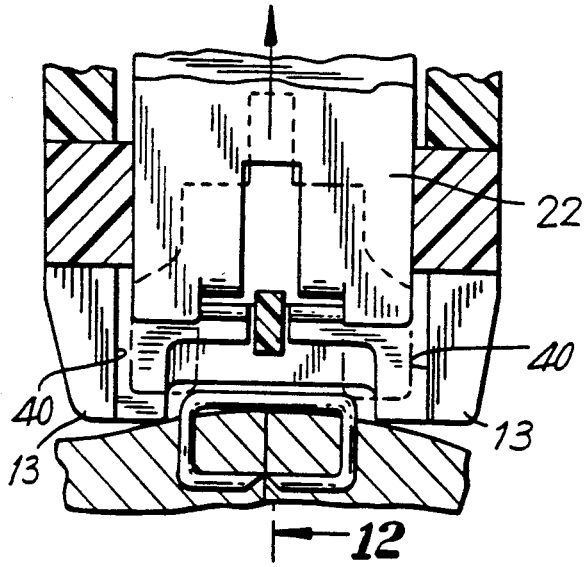
FIG. 11 is a fragmentary front elevational view similar to FIG. 9, showing the stripping operation, whereby the former has risen off the staple and the anvil has risen sufficiently to cam the closed staple off the anvil lips transversely to the right, thus releasing the staple.
Figure 12:
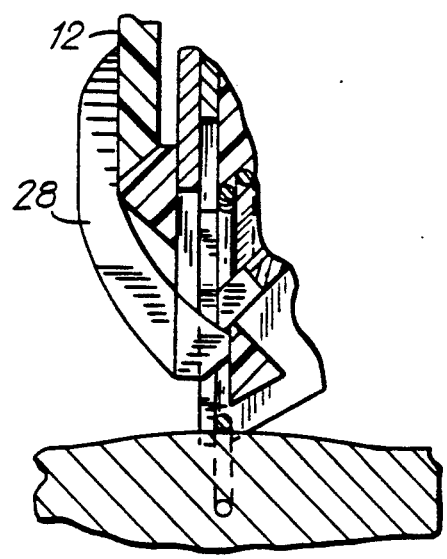
FIG. 12 is a fragmentary sectional view of FIG. 11.

As seen in FIGS. 7 and 8, further downward motion of the former, staple and anvil causes the crossarm to press downward on the flex-tab's bevelled top surface 28C until the flex-tab is resiliently cammed forward and away from the staple cartridge and out of the way of the descending staple, as indicated by dotted line 28E in FIG. 8. When the crossarm descends below the flex-tab, the flex-tab springs back to its relaxed position above and in the path of the staple. During this descent and during further descent of the anvil, staple and former, the flex-tab is not affected by the anvil or former because both have recesses 22C and 20E respectively that allow clearance for the flex-tab.

As seen in FIG. 7 the movement of the staple and anvil from above the flex-tab to below it represents the descent of the anvil to lower the staple to a more visible position below the staple cartridge. This descent distance can be greater if desired.

For convenience of description the descent or downstroke and upstroke will be referred to in stages described as follows.

C. Downstroke Stages

As seen particularly in FIGS. 14A-14D and also in FIGS. 5-8, and FIGS. 16A-16B, the downstroke occurs in stages as described below:

Stage 1—initial "up" position of former and anvil and Stage 2—small descent of former to reach and engage the staple upon anvil lip, as indicated in FIG. 14A.

Stage 3—further descent of former, staple and anvil until staple's crossarm reaches flex-tab, as indicated in FIG. 14B.

Stage 4—further descent of former, staple and anvil as staple crossarm cams flex-tab forward and descends below flex-tab, and anvil reaches anvil downstop.

Stage 5—further descent of former only, as staple is maintained at its descended position by supporting anvil and the former bends the staple legs to closed configuration.

D. Upstroke Stages

Stage 1—initial descended position of anvil and initial fully descended position of former at conclusion of forming staple to closed configuration.

Stage 2—former ascends slightly, disengaging from the staple, while the staple and anvil below it remain below the flex-tab.

Stage 3—former, staple and anvil rise until top of staple cross-arm engages bottom level surface of flex-tab.

Stage 4—the anvil rises very slightly, urging the staple crossarm against the lower bevelled surface of the flex-tab whereby the staple is cammed transversely off the anvil lips.

Stage 5—the anvil rises to its up position stopped by the anvil upstop, and the former rises still further to its top position, leaving space between the anvil lips and the former to receive a new lead staple from the staple mandrel.

E. Downstroke and Staple Closing as Relates to Former and Anvil Springs

The beginning aspects of the downstroke are similar to those of the cited prior art patents. The former is driven downward by pivoting motion of the trigger, with trigger action resisted by force from former spring 24 or anvil spring 26 or both. The structural arrangement of the springs, former and anvil is shown primarily in FIG. 3 with a corresponding force-displacement diagram for the two springs shown in FIG. 13. The up and downstrokes will be described in further detail with respect to both of these figures and other figures when appropriate.

Figure 13:
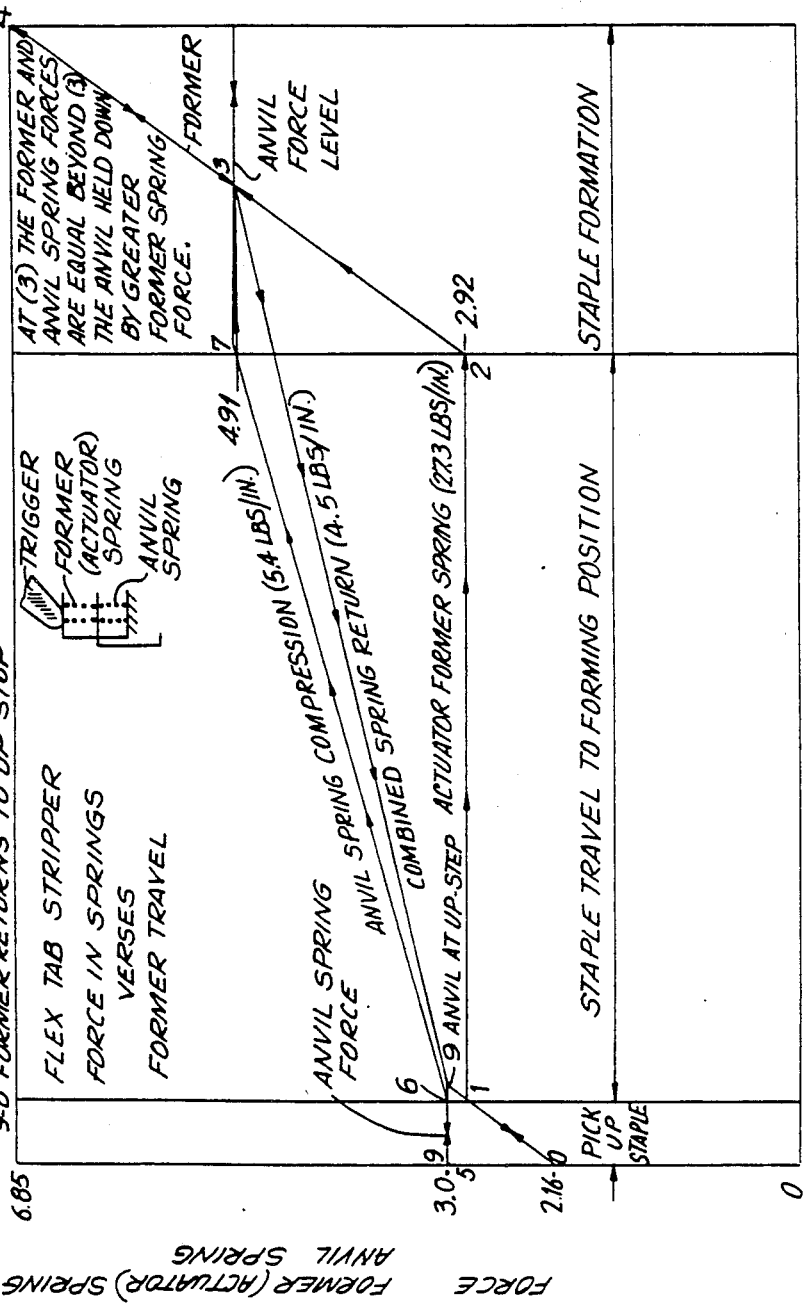
FIG. 13 is a force-displacement diagram for the former and anvil springs.

In the force-displacement diagram of FIG. 13 the lower heavy line represents the force levels of the former spring 24, and the upper heavy line represents the force levels of the anvil spring 26. In the downstroke stages 1-2, the trigger 14 presses directly downward on the former 20. Since anvil spring 26 begins stiffer than former spring 24, the anvil is maintained at its "up" position against its upstop 12B (FIG. 3), while the softer former spring 24 compresses as the former descends slightly until it contacts the staple situated and supported on the anvil lips.

Now the former is in direct contact with the staple upon the anvil, so that in downstroke stage 3 further downward motion of the former, as driven by the trigger, compresses the anvil spring 26, and the former spring remains unchanged in compression, displacement or force. This unchanged spring force is represented by the horizontal line from points 1-2 in FIG. 13. Also in FIG. 13 anvil spring compression is represented from points 6-7 which rises in force as spring 26 is compressed. Note in FIG. 3 the anvil spring bottom part 26B rests against a fixed surface 12C of casing 12, whereas its upper part 26A is pressed downward by anvil arm 22G as the anvil is driven downward by the former against the staple on the anvil lip.

For stage 4 the former, staple and anvil descend further, with the staple crossarm camming the flex-tab forward so that the staple can pass downward to a position just below the flex-tab. Also at this position the anvil has hit its downstop 12A. In FIG. 13 this is indicated by the upper heavy line going from points 3 to 7.

In stage 5, with the anvil stopped, further trigger squeeze causes further descent of the former which compresses its spring (FIG. 13 from points 2-4). As stated earlier, at the beginning of the downstroke, the anvil spring was stiffer than the former spring. Now, however, when the former spring is compressed to point 3, its stiffness rises to equal that of the anvil spring. Movement of the former from points 3-4 causes the former spring to become even stiffer than the anvil spring.

From FIG. 3, it can be seen that the stiffer former spring 24 now presses on anvil arm 22G and holds the anvil down firmly during the former's final descent from points 3-4 as the staple is formed to its closed configuration.

As seen in FIG. 7, the descent in stage 4 positions the staple tips 30E below the lower edge of the stapler, thus substantially improving visibility of the staple for the surgeon. Further details of the downstroke, guidance and closing of the staple will follow a discussion immediately below of the upstroke, stripping and releasing of the closed staple.

F. Upstroke, Stripping and Release

For the return stroke the surgeon relaxes his finger pressure on the trigger, and the former begins to rise, as indicated in FIG. 13 from points 4-3, during which time the former spring is stiffer and thus maintains a downward force on the anvil sufficient to maintain it "down" while the former rises slightly. During this step the former lifts off of the formed staple, leaving it closed around the anvil lip.

The slight ascent by the former is resisted by friction between the former's inner forming surfaces 20D engaging the formed staple's outer surfaces. Due to this frictional engagement the staple will try to stay adhered to the former and rise with it; however, the center part 30F of staple's cross-arm 30B is situated beneath the bottom surface 28B of the flex-tab. Since this flex-tab is fixed to the casing, it has a fixed elevation relative to the rising former and thus bars the staple and the anvil from rising. Consequently the strong former spring force drives the former to separate from the staple.

Shortly after this former-staple separation, the former spring 24 expands and becomes less stiff, the anvil spring force becomes equal to the former spring force, so that the anvil 22 now rises with the former 20 in the continuation of former's upstroke and ascent.

Thus, further ascent is shown in FIG. 13 from points 3-9 where the former and anvil rise together because their respective spring forces are now substantially equal. Note, however, that at point 3 the former has already lifted off the closed staple, but this staple is still below the flex-tab, as further seen in Upstroke-stage 3 of FIG. 14E. In the next stage 4 of ascent, the anvil is initially blocked from rising because the staple's crossarm (above the anvil lips) is trapped under the lower bevelled surface 28B of the flex-tab. Force from the anvil spring, through the anvil lips to the crossarm causes the crossarm to be cammed transversely off the anvil lips. Then the anvil can continue to rise simultaneously with the former, by their equal spring forces, (from point 3 to point 9 in FIG. 13) because both the former and anvil have recesses allowing them to move past the flex-tab even though this tab extends laterally through their recesses.

As seen in FIGS. 5 and 8 a recess 48 is provided for the closed staple to move rearward into when it is cammed off the anvil. At that time the staple is already closed in the wound tissue and easily separates from the stapler.

At point 9 in FIG. 13 the anvil hits its upstop 12B (Fig. 3), and the anvil spring force remains constant until the new cycle. From points 9 to 0 the former 20 continues upward until it hits its own upstop, the former spring force declining as shown from points 9 to 1 as the former spring expands.

G. Flex-Tab's Support To Crown Staple During Closure

A further feature of this new invention is the use of said lower surface 28B of the flex-tab (FIG. 16B) immediately above and adjacent the top center area 30F of the staple's crossarm (FIGS. 16B and 17) while the bottom surface of the crossarm rests upon the anvil lips, and the forming or drive surfaces 20A of the former fingers 20B press downward upon and thereby bend the staple to its final closed configuration.

During such downward bending there is a tendency for the crossarm to bow upward resulting in a poorly formed closure. This is undesirable because the resulting shape will be less stiff as regards forces that tend to open the closed staple, and/or the tips 30E of the staple legs will not bend as tightly closed as is desirable.

With the flex-tab's lower surface 28B above and against or closely adjacent the central area of the top of the crossarm, the central area will be supported or backed-up and barred from bowing upward during the closure stage. Afterwards, as discussed earlier, this lower surface 28B of the flex-tab serves to cam the closed staple off the anvil lips for a quick and clean separation or stripping action.

In this preferred embodiment, as shown in FIGS. 16A, 15A and 15B, the flex-tab's lower bevelled surfaces 28B defines a 30° angle with an axis x—x that lies normal to the axis line of movement of the anvil, and the flex-tab's upper bevelled surface 28C defines a 45° angle with axis x—x. Other dimensions of these surfaces are shown as functions of "d" which equals the diameter of the staple, and "t" which equals the thickness of the anvil. These angles of 30° and 45° have been determined so that in the downstroke the force applied by the staple's crossarm will produce a resultant force vector that cams the flex-tab forward, whereas in the upstroke the force on the staple's crossarm applied to surface 28B will not be great enough to cam the flex-tab forward, and instead the staple's crossarm will itself be cammed rearwardly by surface 28B off the anvil lips.

H. Guidance of the Staple during the Downstroke

To enhance smoothness of operation and reliability against hang-ups, the staple is guided by a variety of surfaces and elements during its descent and closure. When the former begins its descent and engages the staple, the forming surfaces 20A of fingers 20B include concave grooves to restrain the staple from tilting or turning. As long as the staple is captured between the anvil lips below the crossarm and the grooved former surfaces above the staple's upper surface, the staple cannot slip, tilt or twist. This general condition continues during the descent of the anvil, and during the closure by further descent of the former.

During descent of the staple while it is contacted from above and below, there remains the possibility of lateral movement in the direction of the crossarm's axis. If this occurred, the staple would not remain centered on the anvil lips, and downward pressure by the former would produce a misconfigured closure of drive the staple out of its proper location, possibly causing a jam-up. The prevent such lateral movement of the staple, concave grooved guide tracks 40 are provided at the front of casing walls 13 in the plane of the staple when it is driven downward by the former. In the embodiment shown in FIGS. 5 and 7 tracks 40 are provided in plastic guide 42.

Further guidance for the staple during its descent is provided by tabs 22G (FIGS. 4, 7 and 16A) which extend downward on the anvil, adjacent and outward of the lips 22A. These tabs prevent the staple leg parts 30C from swinging forward during descent and even during closure. The staple legs are also guided from swinging rearwardly by guide surfaces 44 seen in FIGS. 3 and 6. In this embodiment surfaces 44 are parts of the cartridge sub-assembly 15 that is installed as a complete unit into the housing 12. This cartridge comprises a frame that carries the mandrel 32 and staples thereon, and supports the former, anvil and their springs. For economy of manufacture this frame is a molded part that accommodates the above-described elements, and is inserted by snap-action between the casing walls 13.

During closure the former fingers' concave grooves remain in contact with the staple until its final closed configuration is achieved, at which time guidance from tipping and/or lateral axial movement are not longer issues. Instead, the only remaining problem is smooth and quick stripping or separation of the closed staple from anvil, which has been solved by the stripper described above.

I. Reducing Dimensional Tolerance Sensitivity

Without the various new features described above, staplers typically require substantially close dimensional tolerances in order to engage, hold, close and release staples without risk of the staple slipping, turning or moving out of its prescribed positions and causing a hang-up of the apparatus. With the new flex-tab that cooperates with the anvil and balanced spring subassembly to provide fast and reliable stripping, combined with the flex-tab's second function of backing-up or crowning the crossarm during closure, the staple is easily positioned and controlled throughout the entire downstroke and also during the upstroke when a new lead staple is delivered to the anvil.

Any or all of the new features of the present invention, namely the new stripper, crossarm crowning bar, and guidance tracks, can be applied to the descending anvil-type stapler as disclosed herein, or to a fixed anvil type, or to a rotating head type of stapler, or to a stapler which rotates each staple as received from the staple magazine before closing the rotated staple.

The invention described herein has focussed upon certain preferred embodiments and features. It is intended, however, that numerous variations and equivalent embodiments be deemed within the spirit and scope of the invention as set forth in the appended claims.

I claim:

1. In a surgical stapler which includes an anvil having a transverse lip for receiving a staple, a former for driving said staple in a downstroke from an initial rest position, and spring means for biasing said former toward its rest position, said staple being bent about the anvil lip during the downstroke, the improvement in combination therewith of a stripper means for stripping the closed staple off the anvil lip, said stripper means comprising a projection from said housing having an end part with a lower cam surface thereon, in operation of said stapler said stripper being positioned such that after the downstroke said end part has its lower cam surface above the crossarm of a closed staple on the anvil lip, and means for urging said lower cam surface against said crossarm which lower cam surface drives said staple transversely off said anvil lip.

2. In a surgical stapler including a housing, an anvil with a transverse lip for supporting the crossarm of a staple, and a former for pressing the bending a staple to its closed state about said anvil lip, the improvement in combination therewith of crowning means carried by the housing and situated above and closely adjacent the staple cross arm while the staple is being formed to its closed state.

3. Apparatus according to claim 2 wherein said crowning means comprises a crowning element movable to a position above and closely adjacent the top central surface of the crossarm at least during the portion of the downstroke when the staple is being closed, and positioning means for positioning said crowning element during said portion of the downstroke.

4. In a surgical stapler which includes a housing, an anvil having a transverse lip for receiving and carrying the crossarm of a staple along a delivery path, a former for driving said anvil and staple in a downstroke from an initial rest position, and spring means for biasing said anvil and former in an upstroke toward their respective rest positions, said staple being bent to a closed state about the anvil lip during the downstroke, the improvement in combination therewith of a crowning mans comprising a projection from said housing having an end part with a lower surface thereon, in operation of said stapler said lower surface being positioned above and closely adjacent the top central surface of the crossarm during the portion of the downstroke while the staple is being formed to its closed state for restraining the center of the crossarm from bowing upward.

5. In a surgical stapler which includes a housing, an anvil having a transverse lip for receiving and carrying a staple along a delivery path, a former for driving said anvil and staple in a downstroke from an initial rest position, and spring means for biasing said anvil and former toward their respective rest positions, said staple having a central crossarm and two downward extending legs, said crossarm being bent about the anvil lip during the downstroke, the improvement in combination therewith of a staple guide track on said housing, said track defining a pair of facing walls spaced apart a distance slightly greater than the width of a staple in open condition, said walls situated lengthwise along the delivery path at a position where the staple is located when bending to its closed state occurs, said walls being centered relative to the center of said anvil lip, whereby said staple crossarm on said lip is prevented from moving axially relative to said lip.

6. Apparatus according to claim 5 wherein said anvil lip extends transversely on a first side thereof, and said former has a body part adjacent said first side, whereby said former lies in the plane of a staple on said lip, and said tracks are in said same plane.

7. Apparatus according to claim 5 wherein said spring means comprises an anvil compression spring and a former compression spring, said springs situated with the anvil spring having one end engaging the housing and its opposite end urging the anvil to its rest position, and the former spring situated between the anvil and the former for urging the former to its rest position, said springs having spring rate characteristics whereby during the beginning of the downstroke the anvil spring is stiffer than the former spring, and during bending of the staple the former spring is stiffer.

8. Apparatus according to claim 7 wherein said housing comprises an upstop and a downstop for limiting movement of the anvil during its upstroke and its downstroke respectively, said anvil and former springs having equal stiffness during the downstroke at a time after the anvil has reached its downstop.

9. Apparatus according to claim 8 wherein the springs have equal stiffness at a point about midway of the portion of the former's downstroke that corresponds to the bending of the staple to its closed state.

10. Apparatus according to claim 7 wherein said springs are coaxial coil springs.

11. Apparatus according to claim 10 wherein said former and anvil are generally flat plate members, each having a transverse arm for the engagement with said springs.

* * * * *